United States Patent [19]

Sackier et al.

[11] Patent Number: 5,612,028

[45] Date of Patent: Mar. 18, 1997

[54] METHOD OF REGENERATING OR REPLACING CARTILAGE TISSUE USING AMNIOTIC CELLS

[75] Inventors: Jonathan M. Sackier, Surrey; Christopher B. Wood, Buckinghamshire; Rajagopallan Krishnan, Surrey; Gordon R. Wiggington, Hampshire; Douglas Mitchel H. Butler, Surrey, all of Great Britain

[73] Assignee: Genethics Limited, Surrey, United Kingdom

[21] Appl. No.: 605,858

[22] Filed: Oct. 17, 1990

Related U.S. Application Data

[63] Continuation of PCT/GB89/00175, Feb. 17, 1989.

[30] Foreign Application Priority Data

Feb. 17, 1988 [GB] United Kingdom ............... 8803697

[51] Int. Cl.$^6$ ........................................ A61K 35/50
[52] U.S. Cl. .................. 424/93.7; 424/582; 623/18; 623/19; 623/20; 623/21
[58] Field of Search ............... 424/93 B, 93 C, 424/93 U, 582, 93.7; 623/1, 11, 12, 13, 18, 19, 20, 21

[56] References Cited

U.S. PATENT DOCUMENTS 4,553,272  11/1985  Mears.
4,820,626   4/1989  Williams et al. ............... 435/1

FOREIGN PATENT DOCUMENTS 0206025  12/1986  European Pat. Off..
0230672   8/1987  European Pat. Off..
2110531   6/1983  United Kingdom.

OTHER PUBLICATIONS

Lyons et al., Laryngoscope 87 (10 Pt 1): 1705–1709 (Oct. 1977) Abstract Medline 78009509.
Walker et al, J. Pediatr Surg. 12(3): 391–395 (Jun. 1977) Abstract Medline 77209413.
Tancer et al., Obslet. Gynecol. 54(3): 345–349 (Sep. 1979) Abstract Medline 79245533.
Tozum, Int J. Gynaecol. Obstet. 14(6): 553–6 (1976) Abstract Medline 78003927.
Scaggiante et al., Transplantation 44(1): 59–61 (Jul. 1987) Abstract Medline 87264787.
Scaggiante et al., Pediatr Med Chir 9(1): 89–92 (Jan.–Feb. 1987) Abstract Medline 87317160.
Wlodarski et al., Arch Immunol. Ther Exp (Warsz) 26(1–6): 1033–1036 (1978) Abst. Medline 79164843.
Wlodarski et al., Arch Immunol. Ther Exp (Warsz) 26 (1–6): 1027–31 (1978) Abstract Medline 79164842.
Wlodarski et al., Exp. Hematol. 8(8): 1016–23 (Sep. 1980) Abstract Medline 81138589.
Wlodarski et al., Calcif. Tissue Res. 5(1): 70–79 (1970) Abstract CA73(9): 43265.
Akle et al., Int J. Biol Res Pregnancy 2(1): 23–7 (1981) Abstract Medline 82188981.
Akle et al., Lancet 2(8254): 1003–5 (Nov. 7, 1981) Abstract Medline 82079471.
Alpin et al., Exp Cell Res 153(2): 425–438 (1984) Abstract BA78:89940.
Heterotopically Induced Bone Marrow Formation: Morphology and Transplantation Exp. Hematol., Sep. 1980, vol. 8, No. 8, pp. 1016–1023.
Investigations on Cartilage and Bone Induction in Mice Grafed with FL* and WISH** Line Human Amniotic Cells, Calc. Tiss. Res. 5, 70–79 (1970).
Permeability of the amniotic membrane and its potential application for transplantation purposes, Biological Research in Pregnancy, vol. 2, No. 1—1981 (pp. 23–27).
Immunogenicity of Human Amniotic Epithelial Cells After Transplantation into Volunteers, The Lancet, 7 Nov. 1981, pp. 1003–1005.
Adhesion of Human Amnion Epithelial Cells to Extracellular Matric, Experimental Cell Research 153 (1984) 425–438.
Implanted Amniotic Membrane as an Autograft and as a Allograft, Journal of Medicine, vol. 6, No. 2, 1975, pp. 169–180.
Amnion Autografts, Permanent Structure, Journal of Medicine, vol. 6, Nos. 3&4, 1975, pp. 243–245.
Morphologic Analysis of Tympanic Membrane Grafts, The Larygoscope 87:1977, pp. 1075–1076.
Use of Fresh Amnion as a Burn Dressing, Journal of Pediatric Surgery, vol. 12, No. 3 (Jun. ), 1977, pp. 391–395.
Vaginal Epithelialization with Human Amnion, vol. 54, No. 3. Sep. 1979, pp. 345–349.
Homotransplantation of the Amniotic Membrane for the Treatment of Congenital Absence of the Vagina, Ing J Gynaecol Obstet 14:553–554, 1976.
Successful Therapy of Niemann–Pick Disease By Implantation of Human Amniotic Membrane, vol. 44, No. 1, pp. 59–61.
Heterotopically Induced Bone Marrow, Archivum Immunologiae ET Therapiae Experimentalis, 1978, 26, 1033.
Heterotopically Induced Bone Marrow, Archivum Immunologiae ET Therapiae Experimentalis 1978, 26, 1027.
The amnion in surgery, past and present, Am. J. Obstet, Gynecol, 134:833–845, 1979.

(List continued on next page.)

*Primary Examiner*—Marian C. Knode
*Assistant Examiner*—Jean C. Witz
*Attorney, Agent, or Firm*—Foley & Lardner

[57] ABSTRACT

This invention is based upon the application of amniotic cells—in particular, viable epithelial cells—to clinical procedures including the treatment of diseased or damaged tissues, e.g. in joints denuded of cartilage and vascular grafts. The invention also provides prosthetic devices which incorporate amniotic cells, and compositions for cosmetic use based upon amniotic cells or cell extracts. A further development uses amniotic cells in the form of a semipermeable membrane, or coated onto, for example, microspheres; these structures act as filtration devices for the removal of toxic materials from, for example, blood or urine.

7 Claims, 6 Drawing Sheets

OTHER PUBLICATIONS

Arthroplasty of Joints Using Amniotic Membrane, M. V. Volkov, Moscow, USSR, pp. 53–56.

Replacement Of The Peritoneum With Amnion Following Pelfic Exenteration, Surgery, Gynecology & Obstetrics—Nov. 1977—vol. 145, pp. 699–701.

Amnioplastin For Adherent Digital Flexor Tendons, The Lancet, Jan. 17, 1942, pp. 70–72.

Amnion Implantation in Peripheral Vascular Disease, British Medical Journal, Aug. 4, 1956, pp. 262–268.

Amniotic Arthroplasty For Tuberculosis Of the Hip, The Journal of Bone and Joint Surgery, vol. 68–B, No. 1, Jan. 1986.

A Review Of The Role Of Amniotic Membranes In Surgical Practice, Richard N. Matthews, W. Page Faulk, and John P. Bennett, pp. 31–59.

METHOD OF REGENERATING OR REPLACING CARTILAGE TISSUE USING AMNIOTIC CELLS

This application is a continuation under 35 USC § 120 and § 365 of PCT application Ser. No. PCT/GB89/00175, filed Feb. 17, 1989.

FIELD OF THE INVENTION

This invention relates to the clinical use of amniotic membrane cells or tissues.

BACKGROUND OF THE INVENTION

The amnion is a unique membrane, composed of a single layer of cells, which completely line the cavity in which the foetus grows and develops. It is formed from the same small group of cells which are formed when the ovum fertilised by the sperm begins to divide. These cells have the potential to develop into all the cells of the human body and under the action of growth factors, and by a process which is as yet undefined, the cells will differentiate into either muscles, bones, heart, liver or whatever structure is required. We now have reason to believe that the cells which go to form the amnion retain this pluripotential characteristic of being able to differentiate, at least in part, into other tissues.

Another unique feature of the amniotic membrane is the complete lack of expression of surface antigens responsible for mounting an immune reaction. Thus, the amnion does not induce an immune response when transplanted into a "foreign" site, a feature which is of major importance to the foetus.

The body's immune system rapidly recognises foreign material and sets up an immune response which rapidly destroys the alien cells or organisms. Such considerations suggest that the fertilised ovum should be recognized by the body as a foreign or "non-self" tissue and be destroyed by the immune system. In fact, the ovum, and later the developing foetus, is spared from the immune response and is able to grow and flourish within the maternal uterus completely protected from the scavenging lymphocytes of the mother's immune system. Although the mechanism is not completely understood, the amnion is the key to the foetal protection. It is the immunological barrier between the mother as the host and the embryo as the "foreign" tissue.

Figure 1:
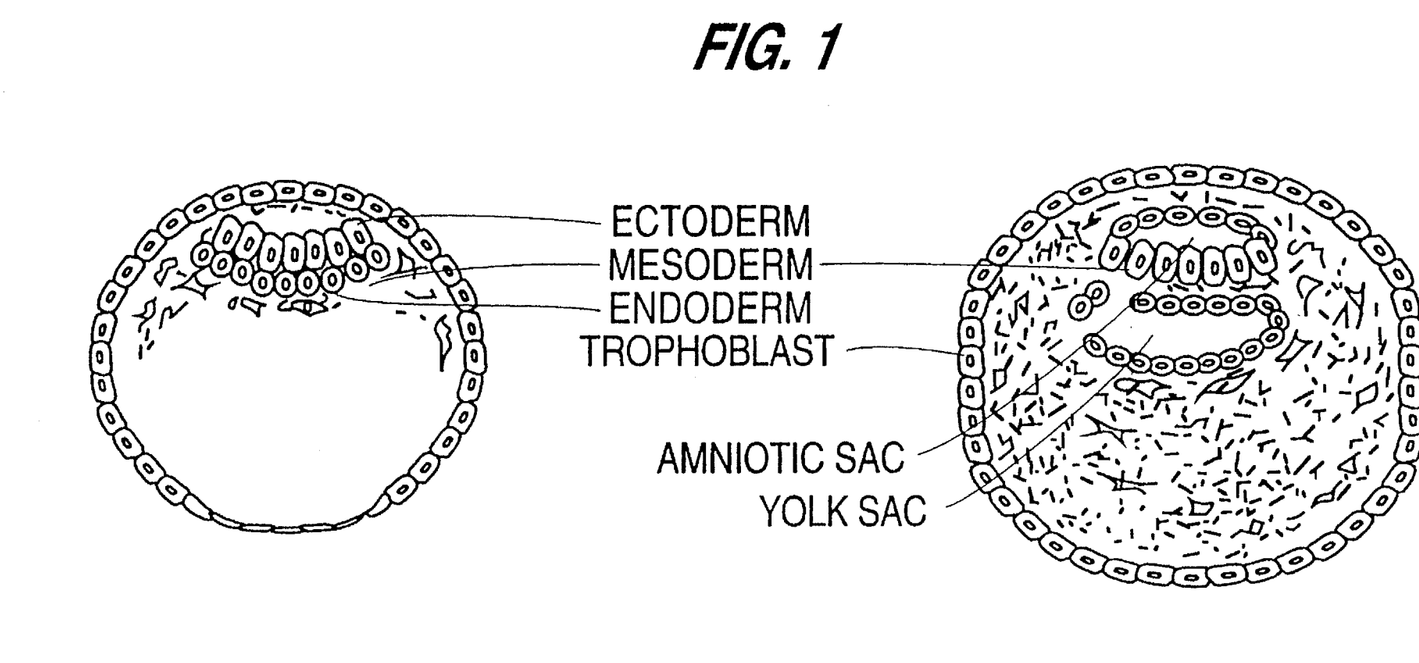
FIGS. 1 to 4 illustrate the stages of development of the human embryo.

While still in the fallopian tube, the fertilised ovum divides repeatedly to form a round mass of cells, the morula, from which develops both the foetus, the placenta and the amnion. It is this central origin of the amnion and its close relationship with the developing embryo that makes the amnion such a fascinating subject for research. An eccentric space appears in the morula resulting in a hollow sphere or blastocyst with a mount of cells on one aspect of the inner surface—the inner cell mass. The outer shell of the blastocyst becomes the trophoblast responsible for nutrition of the embryo (see FIG. 1).

Figure 2:
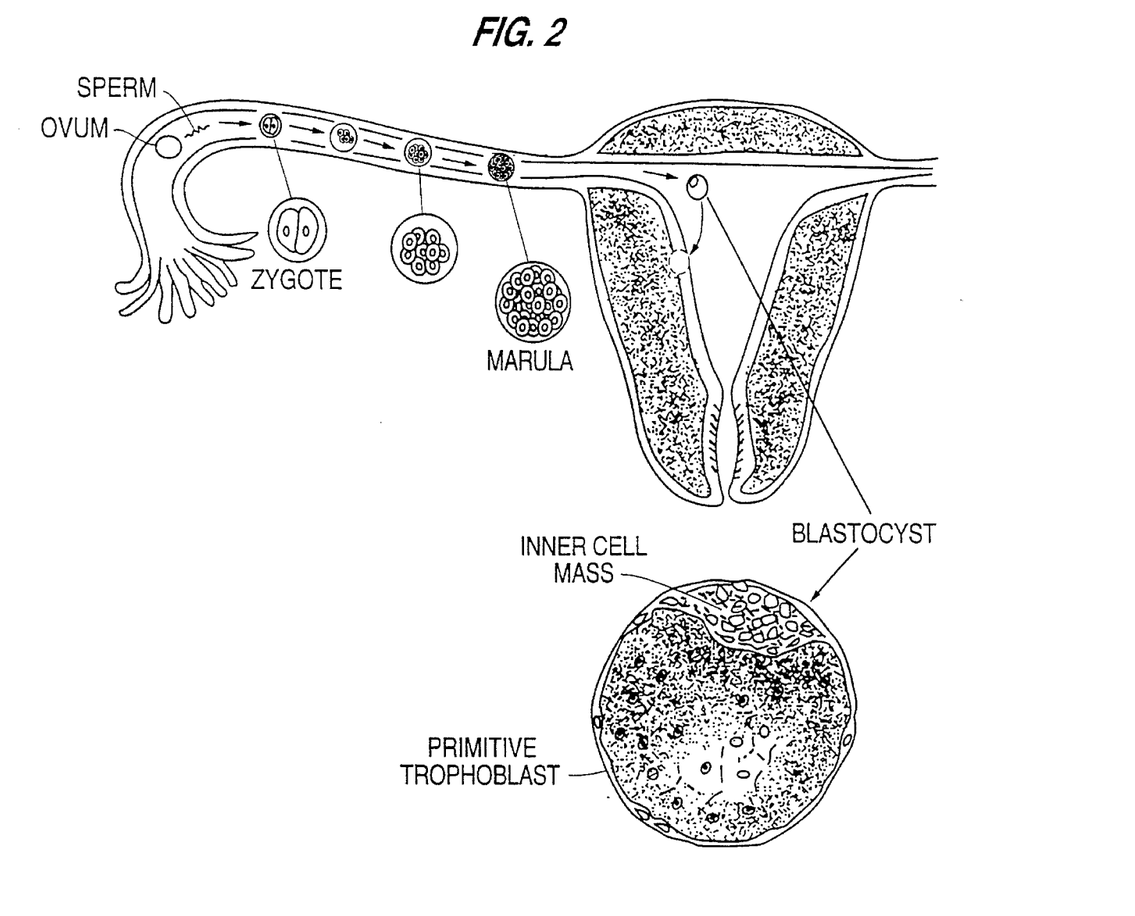
Figure 3:
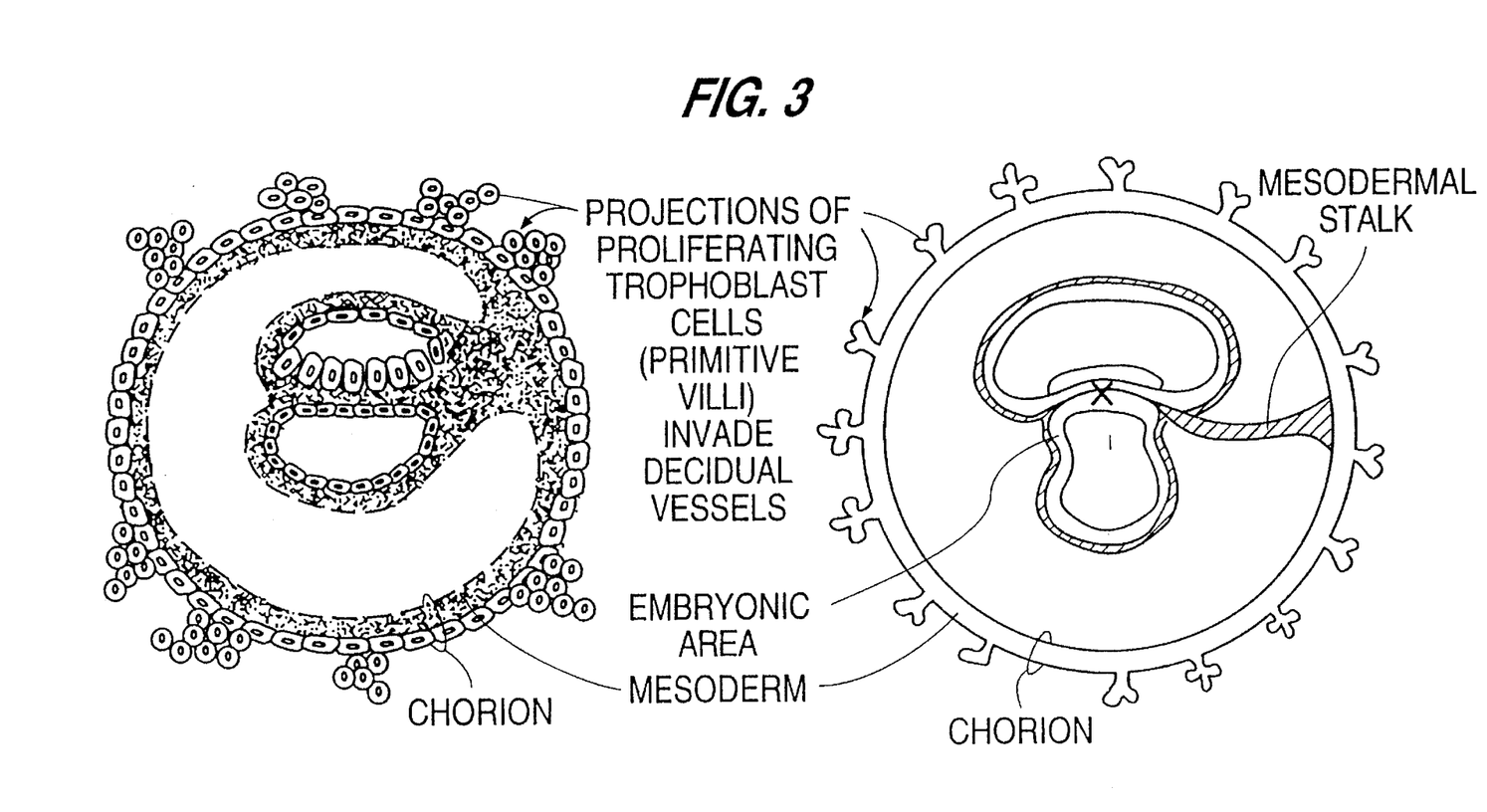

The inner cell mass differentiates and forms two distinct masses, the outer (ectodermal) layer and the inner (endodermal). A further differentiation produces a third layer, the mesoderm, between these two (see FIG. 2). The combination of trophoblast and primitive mesoderm is termed the chorion (see FIG. 3). Two small cavities appear, one in the ectoderm forming the amniotic sac, the other in the endoderm—the yolk sac.

About the twelfth day after fertilization, the amniotic cavity is formed and the embryonic ectoderm of the inner cell mass takes shape from the floor of the amniotic cavity (Hertig 1968), the roof of which is formed by amniotic epithelium (Hertig 1945, Bourne 1942).

As the amniotic cavity continues to expand the amnion reaches the wall of the blastocyst. At the same time it involves the yolk sac. Part of the yolk sac becomes enclosed within the embryo while the remainder forms a vestigial tube which is applied to the original mesodermal stalk.

Figure 4:
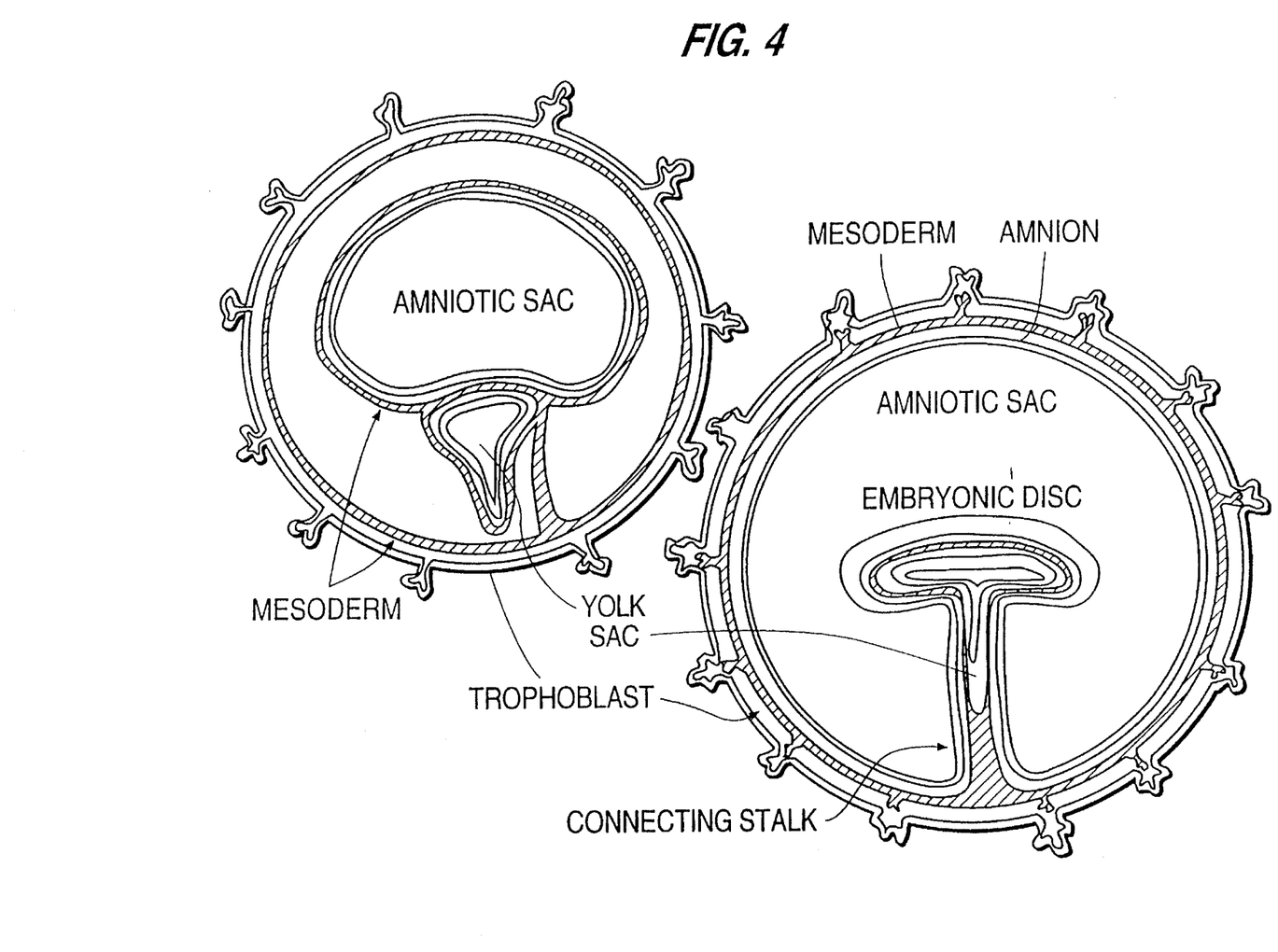

Blood vessels develop in the embryonic mesoderm and in the mesoderm of the trophoblast. Extension of these vessels along the connecting stalk result in the formation of the umbilical arteries and vein (see FIG. 4).

Within the embryo the vessel at the cephalic end differentiates to form the heart. Foetal blood formation occurs within the primitive blood vessels of the trophoblast and foetus. Interchange between mother and foetus is facilitated by the formation of this foeto-trophoblastic circulation. The formation and differentiation of the hemopoietic vascular system occurs between the third and fourth week of pregnancy. From then on full development of the foetus can take place.

Oxygenated blood from the placenta returns to the foetus via the umbilical vein. This vessel penetrates the liver and gives off small branches to that organ. Most of the blood is directed via the ductus venosus into the inferior vena cava which is carrying the returning non-oxygenated blood from the lower limbs, kidneys, liver and other organs. There is only partial mixing of the two blood streams and most of the oxygenated blood is directed by the crista dividens at the upper end of the inferior vena cava through the foramen ovale into the left atrium and thence to the left ventricle and aorta. This relatively well oxygenated blood supplies the head and upper extremities. The remainder of the blood from the superior vena cava mixes with that of the inferior cava, passes to the right ventricle and thence to the pulmonary arteries. A very small amount of blood actually perfuses the lungs. Most of it passes on via the ductus arteriosus into the aorta beyond the vessels supplying the head and other extremities. Thereafter it passes down the aorta to supply the viscera and lower limbs. Little blood actually perfuses the lower limbs. Most at this level passes into the umbilical arteries which arise as branches of the right and left internal iliacs. At birth, the umbilical vessels contract. Breathing helps to create a negative thoracic pressure thus sucking more blood from the pulmonary artery into the lungs and diverting it from the ductus arteriosis which gradually therefore closes. The foramen ovale is a valvular opening, the valve functioning from right to left side of the heart. The left auricular pressure rises and this valve closes.

The primitive trophoblast erodes the surface of the decidua by enzymatic process, destroys the glands and the stroma and eventually, therefore, penetrates large maternal sinusoids which have formed in the lining of the uterus. The blastocyst now lies in a pool of maternal blood fed by the maternal arterioles and drained by maternal veins. The trophoblast cells proliferate and form pseudopodial like masses which branch repeatedly. This greatly increases the surface area and facilitates foeto-maternal exchange. The trophoblast anchors the blastocyst by adhering to the intervening decidual stroma. The trophoblast differentiates into two layers. The outer or syncitiotrophoblast in contact with the maternal blood becomes the multinucleus syncitium with no distinct cell boundaries, the inner or cytotrophoblast (also called the Langhans layer) forms a single layer of cuboidal cells.

Villi are present over the whole surface of the blastocyst. As this enlarges it compresses the superficial decidua or decidua capsularis and the pregnancy bulges into the uterine cavity. The compression of the decidua capsularis gradually cuts off the circulation through it. This results in atrophy and disappearance of the villi in association with it. The surface of the blastocyst becomes smooth and this portion of the chorion is known as the chorion laeve. At the opposite end of the blastocyst the villi proliferate and enlarge and this is known as the chorion frondosum. The connecting stalk of the embryo is attached to the wall of the blastocyst at this point. Ultimately, with the expansion of the blastocyst, the decidua capsularis comes into contact with the decidua vera and the uterine cavity is obliterated.

The fully formed placenta is a disc approximately two centimeters in thickness tapering towards the edges. It weighs roughly 500 grams and is dark red, the colour being due mainly to the maternal blood within the intervillus spaces. The umbilical cord has two arteries and one vein embedded in Whartons jelly which is a loose myxoematus tissue of mesodermal origin. This jelly acts as a physical buffer and prevents kinking of the cord and interference of maternal-foetal circulation.

The umbilical vessels are generally attached to the placenta near its centre. They immediately divide repeatedly to the form branches which ramify all over the surface. This is known as the "disperse" type of placenta. Occasionally the main vessels may extend almost to the margins of the placenta before dividing (although they give off small branches in their course). This is the "magistral" type of placenta. There is a short communicating branch between the two umbilical arteries just as they reach the placental surface. This serves to equalise the pressure and flow to each half of the placenta.

The functions of the placenta depend on the structure and health of the placental villi. These villi are bathed in maternal blood but there is no direct connection between foetal and maternal blood. There is a foeto-placental barrier. After sixteen to twenty weeks the cytotrophoblast regresses. The syncitiotrophoblast is reduced in thickness as the pregnancy advances. The foetal blood vessels of villi dilate and the mesoderm is reduced in amount. This reduces the physical barrier between foetal and maternal circulations. Indeed, at twelve weeks the barrier is 0.025 millimeters and at term is 0.002 millimeters. The placental functions may be summarized as follows:

1. Respiratory

The fall in pressure as the maternal blood enters the placenta and the resulting slow flow aid the foeto-maternal interchange. Maternal blood has a relatively high oxygen and a low carbon dioxide content. The passage of oxygen to the foetus and of carbon dioxide to the mother is thus made easy. In addition it is thought that foetal haemoglobin is more readily able to take up oxygen even when the concentration of maternal oxygen is low.

2. Nutritional

Active transport mechanisms exist in the placenta to aid the exchange of substances between mother and foetus. For instance naturally occurring amino-acids which are laevo-rotatory are transported across the placental barrier more quickly than synthetic dextro-rotatory forms.

3. Endocrine

The placenta produces a number of hormones: oestrogens, progesterone, chorionic gonadotrophin, growth hormone like substances (human chorionic somatotrophin), corticosteroids and post-pituitary like substances. Oestrogens and progesterone are produced mainly by the ovary during the first twelve weeks of pregnancy. During this time chorionic gonadotrophin is secreted by the placenta in large quantities to maintain the corpus luteum. Thereafter, the placenta gradually takes over the production of the oestrogens and progesterone. The corpus luteum regresses and the secretion of chorionic gonadotrophin is greatly reduced.

Oestrogens and progesterones maintain the growth of the uterus and control its activity during pregnancy. They are also responsible for changes in the maternal body such as growth of the breasts.

Similarly, corticosteroids are greatly increased in pregnancy and some are produced by the placenta. They are also involved in alterations of maternal metabolism. A substance resembling posterior pituitary hormone is said to be formed by the placenta. This remains a matter of controversy.

4. Membrane Developments

The membrane is derived from that part of the trophoblast which atrophies as the blastocyst expands—the chorion laeve plus the amnion. The amnion is easily stripped from the chorion and this helps to distinguish dizygotic (binovular) from monozygotic (monovular) twins. If the membranes are in three distinct layers over the surface in apposition, the twins may be either monovular or binovular. When the membranes in apposition consist only of two layers, the two amnions, the twins are definitely monovular.

5. Amniotic Fluid

The volume of this fluid increases up to the thirty eighth week, falls slightly up to term and then more rapidly thereafter. The fluid is replaced every three hours and its formation and circulation is still a subject of research. It may be derived from a variety of sources. The composition of the fluid is not simple; it is not merely a transudate. The concentrations of substances are seldom the same as found in maternal plasma although some may rise and fall in concert with maternal blood. A variety of hormones are to be found in the fluid—chorionic gonadotrophin, placental somatotrophic hormone, oestrogens, progesterone and hydroxycorticosteroids are found in varying quantities. Prostoglandins of two types are found. Type E is found in early pregnancy whereas at term it is type F which is present in most abundance. In addition a large number of enzymes have been demonstrated in amniotic fluid and its cells. A number of cell types can be found floating within the fluid during early pregnancy—large eosinophils, large basophils and small basophils. These are derived from foetal skin, mouth, vagina and bladder. After the thirty sixth week anucleate polygonal eosinophilic cells are found which stain orange with Nile blue sulphate and which are squames from foetal skin. The amniotic fluid may be visualised through the membranes using an amnioscope. In addition amniocentesis or withdrawal of the fluid, is now a common procedure. Chemical estimations and microscopical studies may be made for the following purposes.
1. Prognostication in cases of rhesus incompatibility by determining the bilirubin content.
2. Determination of the lecithin/sphyngomyelin ratio which increases as the foetal lung matures.

3. Antenatal sex determination in cases of suspected sex linked disorders.
4. Detection of chromosomal abnormalities.
5. Diagnosis of foetal storage disorders.
6. Diagnosis of foetal enzyme deficiencies.

The chromosomes and their constituent genes ultimately determine the characteristics of each individual. The cells of any individual produce a variety of proteins and mucopolysaccharides which exist as markers on the surface and interiors of cells and these markers are known as antigens. When a body is exposed to foreign antigens i.e. antigens which do not exist within that tissue under normal circumstances, the body recognises these as foreign and produces antibodies.

These antibodies attach onto the antigens much as a key fits a lock. The net result of this recognition is the destruction of the foreign material. A good example of this function is with blood grouping into the AB system. For instance, if a person is blood group A then on the surface of their blood cells they bear the A antigen. If blood which is of blood group A is transfused into that patient, then the body does not recognise it as a foreign and the transfusion is accepted—this is the basis for nationalised blood transfusion services. However, if blood of group B is infused into the same patient, this blood contains B antigens on the surface of the red cells and within the transfused blood there are antibodies to blood group A. In addition, the recipient of the blood transfusion will have circulating within his plasma antibodies to blood group B. The result of this erroneous transfusion is that, the small amount of transfused anti-A damages the recipients cells, but more importantly the recipient recognises the B antigen on the transfused cells and promptly destroys them. This leads to a florid transfusion reaction which in dire circumstances can lead to the death of the patient and is well characterised in history when blood transfusions were first attempted.

There are in fact numerous blood group antigens and consequently blood cross matching is a time consuming expert process. The same techniques have been used to "type" organs for transplantations such as kidneys, livers, hearts and lungs. If a close match is obtained then the results may be quite good; these are assisted by giving immunosuppressive drugs which are substances that quell the immune reaction in the recipient but which also open up the patient to opportunistic infections and the development of certain cancers. Thus, if one were to transplant a kidney that was not well matched, the recipient would reject this organ within twenty-four hours and it would not function, whereas a kidney donated by an identical monovular twin would be perfectly acceptable since the kidneys of both the donor have originated from the same ovum and sperm.

An unusual characteristic of amnion epithelial cells is their apparent failure to express Class 1 histocompatibility antigens (HLA -ABC) in a form or density that can be identified immunohistologically (Hsi 1982, Adinolfi 1982). Amnion cells also appear to be negative for Class 2 (HLA -D antigen) antigens. At present, the reasons for failure of amnion cells to express histocompatibility antigens in a normal manner are not known but possible explanations include:
1. Genes for the expression of class 1 antigens may be deleted.
2. Genes may be defective.
3. Genes may be "down regulated" by positive or negative control mechanisms (Hunt & Wood 1986).

Hunt and Wood suggested that failure of transcription may be responsible for failure of normal expression of Class 1 HLA antigens and beta 2 microglobulin by cells of the amniotic epithelium although production of minute quantities of these antigens has been noted with sensitive radiological techniques (Adinolfi 1982). This does not appear to cause a problem after transplantation.

Reports on the immunogenicity of human amniotic epithelial cells after transplantation into human volunteers have been published (AKle 1981, Adinolofi 1982). Pieces of amnion consisting of a mono-layer of epithelium on a basement membrane with an underlying collagen matrix containing a few fibroblasts (which in theory would express the HLA antigens, although the epithelium itself lacks the antigens) were transplanted into subcutaneous pouches in normal human volunteers.

None of the volunteers showed clinical signs of acute rejection and amniotic epithelium cells were demonstrated by biopsy up to seven weeks after implantation. HLA antibodies were not detected in serum samples and there was no in vitro lymphocyte reaction to the amniotic cells in two of the volunteers. The results suggest that acute immune rejection does not occur after the allotransplantation of human amniotic epithelial cells. These authors suggest that if there was an immune response to the graft, it is certainly low grade and chronic rather than active and it is clearly ineffective since the amniotic epithelial cells appear to survive and even in some cases to proliferate (AKle 1981, Adinolfi 1982).

In transplantation of human organs, whether skin, kidney or liver etc., the major problem is rejection of the grafted tissue due to the immune response. Amnion has been used successfully as a skin graft without having to worry about correct tissue typing and matching of the donor to the host.

In addition to acting as the immunological barrier the amnion also functions in a number of other ways on behalf of the foetus. Whilst in the uterus, and particularly during the early stages of development, the embryonic kidneys are unable to deal adequately with fluid balance and waste product disposal. These functions are controlled by the amniotic membrane and several litres of fluid are exchanged between the foetus, the amniotic cavity and the mother during the course of each day. In addition, urea, which is one of the major waste products, is actively transported across and amnion. Recent evidence has shown that to all intents and purposes the amnion acts as a simple kidney (Lingwood and Wintour 1983).

All human cells excluding the sex cells and the red blood cells possess all the genetic information required for the complete human being.However, taken out of their usual situation in the body a cell only has the ability to regenerate the tissue from whence it came. Different tissues have different regenerative capabilities, the liver for instance being extremely good, the central nervous system almost non-existent.

Foetal membranes have been put to a variety of surgical membranes for skin coverage in the past. Stern (1913) and Sabella (1913)used amnion for treating burns and skin ulcers and reported relief off pain, increased rate of epithelialisation and no infection. There have been several more recent reports on the use of amnion as a temporary dressing for ulcers, burns and other denuded areas (Tronsegaard-Hansen 1950, Robson, 1973, Robson 1974). stored and desiccated membranes have not been found to offer any significant improvements over other more conventional sterile dressings. But when applied fresh or following preservation at 4° centigrade in isotonic saline, the amnion appears to have advantages which have been reported to include reduction in bacterial counts, relief of pain and hastened healing (Trelford 1975). The amnion has been postulated as producing factors which promote granulation tissue formation, neovascularisation and re-epithelialisation although this is a controversial area(Trelford 1975, (1,2,3) Walker 1977, Faulk 1980).

Other reported surgical uses of the human amnion include its successful application in the repair of conjunctival defects (De Roth 1940); as a replacement for parietal peritoneum (Massee 1962) and to line the pelvic floor after radical exenterations (Trelford-Sauder 1979). Volkov (1973) reported the use of human amnion for arthroplasty in forty four patients with congenital dislocation of the hip with consistently good results; Vishwakarma (1986) reported success with the use of human amnion for arthroplasty in twenty eight patients with tuberculosis of the hip; and Ray et al (1986) reported the use of human amnion for microvascular interpositional grafts in rats with extremely favourable results. However these authors (Volkov 1973, Vishwakarma 1986, Gray 1986) processed the amnion prior to transplantation by techniques which either killed the cells or de-epithelialised the amnion leaving only the mesenchyme. In contrast the basis for the present invention is the use of the live amnion cells, e.g. preserved and grown in sterile tissue culture.

From the discussion above, it will be appreciated that amniotic cells were known to be pluripotential in their natural state i.e. during formation of the foetus. It was also known that human allografts of amniotic cells generated no significant immunological problems.

SUMMARY OF THE INVENTION

We have now found that human amnion can be transplanted into the rabbit knee joint, rabbit Achilles tendon and into rat livers and abdominal cavity without inducing a major immune response. This is a most remarkable phenomenon since the transplantation of any other human tissue into these sites would lead to the almost immediate destruction of the grafted organ or tissue. Furthermore, we have found that the amnion becomes incorporated into, and becomes part of, the host tissue. This remarkable result could not have been predicted and was not expected. We have further found that the amnion induces healing of ruptured tendon and in time is indistinguishable from the original tendon. Accordingly, in one aspect the present invention provides the use of human or animal amniotic cells to regenerate or replace diseased or damaged tissue. This may be done by direct implantation of amniotic cells into the treatment site or, in certain conditions, by the formation of prosthetic devices containing amniotic cells which are then emplaced conventionally.

According to a second aspect of the invention, there is provided a composite implant for surgical use, which comprises a prosthesis which is coated and/or laminated and/or infused with amniotic cells or tissue.

In vascular surgery, prosthetic grafts currently available are usually successful in aortic or aortoiliac surgery, are able to withstand the large pressures generated and thrombosis of the graft is not a major problem almost certainly due to the high velocity flow. However, peripheral vascular areas such as the femoro-popliteal segment or distal vessels generally, present a major problem to grafts whether it is the saphenous vein (which is subject to poor user handling) or prosthetic grafts of PTFE and dacron which are used, since thrombosis limits the success of the operation. The extensive use of coronary bypass surgery is completely reliant upon the quality of long saphenous vein harvested and its handling at operation. The incidence of peripheral vascular operations in the United Kingdom is approximately 4.1 per 10,000 population per annum and approximately 25,000 coronary artery bypass procedures are performed every year, with similar rates of procedures worldwide.

Another problem area is in hepatobiliary surgery, where currently available surgical options for benign and malignant strictures may not always be feasible in district general hospitals. A reliable posthetic graft to bridge a stenotic gap or to repair a damaged duct would help tackle many problems. Cholecystectomies are performed in approximately 7 per 10,000 population per annum and 1.7 per 10,000 population have operations on the ductal system each year in the UK.

In the following description, reference is made to the use of human amnion, although it is to be understood that the invention is not restricted to the use only of human amnion. The human amnion is easily obtained in the fresh state from caesarean sections in the maternity wards, and can be kept in organ culture. The option for making a composite implant is to use intact living sheets of amnion. We have developed methods for layering the intact amnion on to the surface of prosthetic grafts in order to form a lining in the graft lumen.

Although difficult, it is possible to place full-though sutures on sheets of amnion and fashion an amnion tube within the lumen of a preformed prosthesis. To prevent delamination or dissection of the amnion layer from the graft wall, fibrin glue can be used to promote adhesion. Another method is layering of intact amnion on the surface of sheets of woven dacron and then fashioning a tube of the composite. This is certainly feasible and less difficult than the first technique.

A further option for producing a composite implant in the event of practical problems with intact amnion, is to use disaggregated amniotic epithelial cells for seeding the lumen of prosthetic grafts. We have devised this method as an alternative to intact amnion. The luminal surface of a dacron tube can be seeded with vast quantities of disaggregated amniotic epithelial cells (in contrast to vascular or capillary endothelial cells where harvesting the cells in such quantities is a problem) which can then be allowed to grow to confluence in tissue culture in vitro. The time factor to confluence and the prosthesis dimension need to be considered but the technique is feasible and is an alternative method.

Because of the pluripotential capacity of amnion cells, they may be stimulated to regenerate body organ tissues, generate hormones, neuro-transmitters, endocrine and exocrine secretions, and for the producing of monoclonal and polyclonal antibodies. Accordingly, in a third aspect, the present invention provides a method of producing biologically active an/or clinically valuable substances, which is characterised in that said substances are produced from amniotic cells or tissues.

According to a further aspect of the present invention, there is provided a method of regenerating or replacing diseased or damaged tissue in vivo, which comprises introducing into the site of disease or damage human or animal amniotic cells.

The amniotic cells for use in this invention are preferably viable cells, either fresh or after tissue or cell culture in appropriate media. The amniotic cells or tissue may be used directly, or after application to an intermediate material, e.g. a prosthesis or a biologically acceptable carrier, e.g. microspheres of, for example, sepharose.

This invention also provides a system for filtration of toxic material from a biological fluid, e.g. from blood or plasma or serum or urine, which comprises a semi-permeable membrane formed from or inculcated with viable amniotic epithelial cells. In a second filtration system provided by this invention, the amniotic epithelial cells are coated onto suitable carriers and the fluid which is to be treated is then caused to flow over the carriers, e.g. microspheres or beads.

This invention also provides an ointment, cream, lotion or gel containing amniotic epithelial cells or extracts therefrom, dispersed in a suitable carrier, e.g. a pharmaceutically acceptable carrier. A method of treating the skin and/or the scalp using such an ointment, cream, lotion or gel is also provided.

Reference is made to the above drawings at various points throughout the present application.

DETAILED DESCRIPTION

Our latest work transplanting rabbit amnion into rabbit knee joints from which the cartilage has become completely excised, has shown that the amnion becomes firmly incorporated into the joint, a complete layer of new cartilage is formed and the amnion acts as the synovial membrane protecting and lubricating the joint surface. These dramatic changes do not occur in the absence of the amnion. We have found abundant evidence to show that amnion cells are capable of repairing the damage done to the joints by osteo or rheumatoid arthritis.

It has been noted for many centuries that one of the more unusual features of amnion is the way in which blood clots will not adhere to its surface. For some reason the amnion is non-thrombogenic and blood clots slide off the amnion which is in complete contrast to any other cell membrane in the body. We believe that this serendipitous finding can be used to great advantage in situations where blood clotting is a major problem.

Whenever synthetic grafts are used to repair damaged blood vessels they are prone to silting up by blood clots. This is particularly true with the small diameter synthetic grafts and it is for this reason these grafts cannot be used for replacing coronary arteries, an operation which has become one of the most common surgical procedures performed in the western world. In coronary artery by-pass grafting, segments of artery or vein from the patient himself have to be used. Vessels from other donors cannot be used because of the probability of rejection and even vessels from the host are still not free from the danger of thrombosis or clot formation.

We have found that the unique features of the amnion can be put to good effect in the formation of small diameter vascular grafts or for lining existing synthetic grafts with a non-immunogenic, non-thrombogenic surface.

Orthopaedic Surgery

Figure 5:
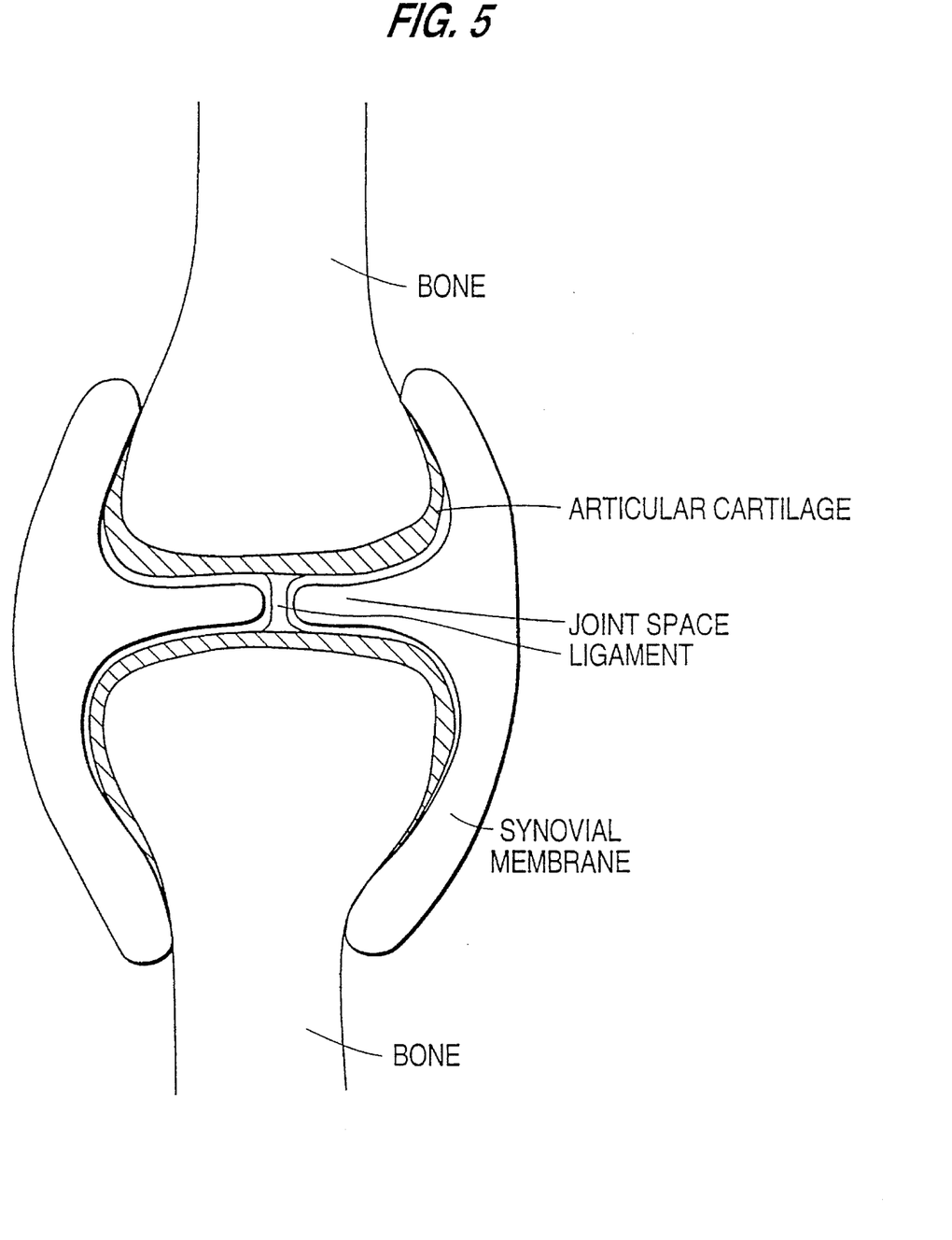
FIG. 5 illustrates the human knee joint.

Every joint in the human body has a similar base structure—consisting of two bones lined with cartilage and a synovial membrane enclosed within a joint space and containing synovial fluid which acts as a lubricant and shock absorber. A number of ligaments provide rigidity and stability and muscles cross the joint to provide movement and also to assist with stability (see FIG. 5). A number of disease processes interfere with the structure and function of joints and many do this by destroying the cartilage and synovial membrane.

Such "arthritis" merely means inflammation of a joint. It may be primary, in which case the cause is not immediately obvious; an example of this would be osteo-arthrosis or "wear and tear" arthritis which is usually a reflection of old age. In addition, rheumatoid arthritis is an immune disease which leads to the auto-destruction of the synovium thereby exposing bone which rubs against its opposite number leading to secondary osteo-arthrosis. A number of infective conditions such as tuberculosis have the same effect.

If the causative disease process is halted by rest, weight loss, altered gait or drugs in the case of rheumatoid arthritis, then there may be no further progression, but that damage which has been done will not repair itself and may well get worse.

Biotechnology has led to some startling developments, not the least of which is the development of prosthetic joints usually fashioned from metals and high impact plastics which are used to replace the damaged bone. These operative procedures are extremely expensive—some hip prostheses costing thousands of pounds. The operations take a long time to perform and the long term results are not always satisfactory, the constituents of the joint wearing out much as the replaced bone had done.

We have tested the use of amniotic epithelium to replace the damaged synovium and cartilage and have found that this is a viable alternative to current treatment options.

In the research work that we have undertaken so far, sheets of amnion have been sutured over denuded and damaged joints but this technique may not be practical for widespread clinical application.

The two published reports (Volkov 1973 and Vishwakarma 1986) on the use of amnion for arthroplasty employ a common technique, first described by Volkov. Amniotic membrane was obtained from the labour ward and washed in running tap water for ten minutes (not isotonic saline). The amnion was then denuded of mucus and mesenchyme by mechanical scraping with razor blades, then cut into pieces of appropriate size (for transplantation into the dog or human hip joint), mounted in multiple layers on glass moulds, dried for six to eight hours or longer at room temperature and the dried caps were then sterilised in 1% beta propriolactona.

The work done in New Delhi on amniotic arthroplasty for tuberculosis of the hip was basically a refinement of Volkov's technique and no visibility studies were performed on the processed amnion (Krishnan 1980, Vishwakarma and Krishnan 1981, Vishwakarma 1986). A careful scrutiny of the preceding technique of amnion processing reveals that every single procedure would make it more and more difficult for the amnion cells to survive. Washing in tap water, mechanical scraping, drying and then sterilization in beta propriolactone kills every cell and in effect the amnion grafts used by Volkov (1973) and Vishwakarma (1986) were all non viable.

This fact has been confirmed by current studies (Krishnan, unpublished data) on amnion processing in similar fashion. However, clinical results have been encouraging despite the use of non-viable grafts in both reports and a possible explanation will be discussed later.

The other relevant report by Gray et al (1986) on the use of human amnion for microvascular grafts in rats employs a totally different technique for amnion processing. The peeled amnion was washed with distilled water to remove mucus and blood and then treated with 0.25% trypsin for two hours to de-epithelialise the membrane which was then placed in 1% phosphate buffered gluteraldehyde at 4° C. for twenty four hours. The membranes were then stored in 70% isopropyl alcohol at 4° C. until graft manufacture. It is obvious that these researchers have not used the amnion in the real sense. In their graft the epithelium (which is the non-immunogenic component and a more suitable material) was actually removed by trypsinisation and therefore the graft almost certainly consisted of acellular amniotic mesenchyme with a few fibroblasts (which are very highly immunogenic since they carry HLA antigens).

Again the fact that the authors obtained good results with remarkable re-endothelialisation of the graft (Gray et al 1986) with little evidence of inflammatory response (a detailed discussion of an immune response, if any, was lacking in the report and immunohistologic techniques to identify cell origin were not performed) can be attributed to various factors. Gluteraldehyde fixation would presumably reduce antigenicity (as occurs with porcine heart valve) and thus the lack of any significant cellular response to human amnion mesenchyme transplanted in the rat. Further, the mesenchyme may have an inductive effect on host endothelial cells.

In our experiments involving direct implantation of living human amnion cells into damaged rabbit knee joints, control animals almost universally have significant restriction of motion in the knee and this is a feature from the very early stages after surgery. At autopsy intra-articular fibrosis and adhesions are a prominent feature in the control knee joint; the articular surfaces are raw and inflamed in most cases and in long term follow up animals the joint is distinctly arthritic. In contrast, loss or restriction of motion is rare in the treated knee joints. Motion is well preserved and comparable to the normal in these joints. Intra-articular adhesions are not a feature of the treated joints.

Non viable human amnion discs appear to remain physically intact for several months in the joint. Histological evidence of the amnion (non viable human amnion group) has been observed for several months and the longest follow up available is one year post-operatively. There has been no evidence of acute, overt graft rejection in the case of non viable amnion transplants. Fibrovascular reparative granulation tissue is prominent in the basal layers of non viable human amnion suggesting organisation of this graft.

There is evidence of cartilaginous regeneration on the articular surfaces subadjacent to the deepest layer of dead human amnion observed at four to six weeks after surgery and more prominent with longer follow up. This suggests the possibility (since the feature of cartilage regeneration is minimal in control joints) that the dead amnion discs provide a mechanical protective "cushioning" effect to regenerating host cartilage (which presumably derives from stem cells in the marrow). It has been noted that live human amnion does appear to provoke a very low grade immune response in sub-cutaneous implant specimens at six weeks. However, we must remember that this is within the rabbit, which bears no similarity to humans whatsoever.

Again, live human amnion layers appear to remain physically intact for several weeks, the longest follow up available being two months after knee joint surgery. A large number of articular specimens are currently decalcifying in EDTA and detailed histology of live human and live rabbit amnion transplant specimens will soon be available.

Tendon covering experiments with live human amnion indicate that in contrast to control tendon repairs (without amnion cover) which develop massive adhesions to adjacent tissue and skin, the amnion covered tendons are smooth and free of adhesions. This is reflected in the clinical setting whereby they have full range of movement and freedom from abnormal gait. Both tendon and sub-cutaneous implant specimens of live human amnion group present evidence of immune response to the amnion but in some instances the amniotic epithelium appears to have proliferated.

However, if the assumption is accepted that the transplanted dead amniotic caps function as inert biocompatible non-immunogenic and non-viable foreign bodies then one would expect to see the process of organisation and eventual degradation which as most clearly not been seen. The host response (that is the amniotic cap sub-chondral bone interface in the joint) of fibrovascular granulation tissue formation, would, with the passage of time, provide a suitable matrix for metaplastic fibro-cartilage of host tissue origin, supplemented perhaps by the incorporation of peptides of degraded and organised non viable amniotic membrane layer.

Another and even more important possibility is cartilage regeneration from pluripotential stem cells in the sub-chondral bone marrow (which would be exposed to the surface by the reaming of the femoral head and acetabulum as part of the standard surgical procedure in previous reports and which is now well accepted as a mechanism for cartilage repair).

Wedge (1986) demonstrated such cartilage regeneration in denuded dog hip joints by the simple expedient of interposing a synthetic biodegradable polymer cap made of poly-1-lactide into the dog hip between the raw femoral head and acetabular surfaces. He suggested that the polymer cap functioned as an inert biocompatible and biodegradable cushion in the joint and provided a mechanical protective effect to the regenerating cartilage which was otherwise an aborted response in control experiments. Similar observations have been made in current studies (Krishnan unpublished data) using dead human amnion discs in rabbit knee joints but will need further substantiation. There is also the suggestion that some components of the amnion may have contributed an inductive influence to enhance host cartilage regeneration.

It is evident from the work carried out in New Delhi that the transplantation of amnion discs into human hip joints, affected with tuberculosis provoked arthritis, is extremely successful in relieving pain and providing mobility to this group of patients. It therefore seems obvious that if dead amnions were merely working as a protective cushion then very soon after the initial good response the situation would be grave as the cushion was destroyed by the action of the joint.

Monoclonal antibody work conducted under our auspices has demonstrated that, in rabbits treated with live rabbit amnion the cartilagenous regrowth originates not from the host bone as has been originally thought, but from the live rabbit amnion.

Our preliminary results of rabbit amnion transplants in cartilage denuded rabbit knee joints are extremely exciting. The findings included full range of motion in the knee, absence of intra-articular adhesions, intact rabbit amnion layers in situ and most encouraging of all, visual evidence of consistent and widespread cartilaginous coverage of the denuded articular surfaces. The rabbit amnion layers were intimately joined to the cartilaginous areas suggesting two possibilities:

a) host cartilage regeneration by induction adding further weight of evidence against mere mechanical protection
b) cartilaginous metaplasia of rabbit amnion itself, since cross species differences do not apply. Five such rabbits have been sacrificed and all five present similar findings. Histology confirms the nature of this substance as cartilage and immunological studies will confirm the fate of the rabbit amnion. We have already conducted a large number of further experiments and the results will shortly be available. Clinically, these animals are all well with full range of motion in the joints.

We have thus demonstrated that live amnion successfully produces cartilaginous regeneration in destroyed joints.

EXAMPLE 1

Rabbit or human or other species amnion is harvested by caesarian section and when rabbits were used, time mated pregnant animals were chosen at twenty seven to twenty eight days of gestation. The multiple membranes from each gestation sac are maintained in tissue culture medium, viability tests performed using promodeoxyuradine as a marker. Viable amniotic membranes are transfixed and sutured to the particular tissues in transplant experiments.

After aplastic experiments were performed in the right knee joint of rabbits and the standard operation was employed throughout, the ligaments were preserved intact and the joints were completely denuded of articular cartilage. The procedures thereafter differed only in respect of the material interposed into the joints. The knee joint experiments consisted of the following groups:

a) controls in which only cartilage was excised —17 rabbits
b) transplants of multilayered discs of processed non-viable human amnion—31 rabbits
c) transplants of viable human amnion—31 rabbits
d) transplants of viable rabbit amnion—29 rabbits
e) implant of inert biodegradable polymer sheeting in the knee joint—7 rabbits Joints were stable after surgery and unrestricted activity was permitted in most instances.

Tendon experiments were performed on 22 rabbits and the procedure entailed the division of the plantaris longus and Achilles tendons after excision of tendon sheaths, followed by repair of the tendons and short term plaster splintage. Follow up studies included comparative assessment of range of motion in ipsilateral operated and contralateral normal joints in each animal and comparison between control and transplant joints. Treadmill experiments were designed which entailed placing rabbits on a purpose built treadmill and making video films of motion in both hind limbs, followed by video digitisation for computer enhanced analysis of gait pattern.

Autopsy studies included exposure of previously operated sites and close examination, followed by an on block resection of the joint and other specimens. Slices of distal femur and proximal tibia were cut for slow decalcification in ethylene diamine tetra acetic acid (EDTA).

Specimens were then frozen or snap frozen for cryostat sections in histology. Histological studies included routine staining with haematoxylin and eosin and toluidine blue and immunohistology. Various monoclonal antibodies to different components of human amnion and other monoclonal and polyclonal antibodies were used.

FOLLOW UP RESULTS

Knee Experiments—Control

| Period of Follow up | Range from 1 week to 15 months |
|---|---|
| Number of rabbits | 17 Fatalities - none |
| Number Autopsied | 17 Infections - none |

Joint Motion—Restriction of movements from early stages. Progressive stiffness at longer follow up. Loss of extension ranged from 10° to 45°. Mean 23.53; S.D.=9.81; S.E.M.=2.38.

Gross Findings—Intra-articular adhesions and fibrosis. Several joints disorganised and arthritic.

Histology—Fibrous tissue on articular surfaces. Minimal evidence of cartilage islands. No significant neochondrogenesis.

Knee Experiments—Dead Human Amnion

| Period of Follow up | Range from 1 week to 20 months |
|---|---|
| Number of Rabbits | 31 Fatalities - 3 |
| Number Autopsied | 27 Infections - 2 |

Joint Motion—Initial postoperative restriction of ROM. Near normal ROM regained at 3–4 weeks. Loss of extension ranged from 0° to 15°. Mean=5, S.D.—4.6; S.E.M.= 0.89

Gross Findings—Little or no intra-articular adhesions. Amnion discs observed up to 4–6 months. Joint surfaces smooth in several cases but not in the lateral half of the joint.

Histology—Amniotic tissue remnants seen up to 1 year. No overt evidence of rejection, mostly eosinophil and polymorph infiltration. Some evidence of neochondrogenesis, mainly a process of organisation.

Knee Experiments—Viable Human Amnion

| Period of Follow up | Range from 1 week to 12 months |
|---|---|
| Number of Rabbits | 31 Fatalities - 3 |
| Number Autopsied | 26 Infections - 2 |

Joint Motion—Virtually normal ROM in most rabbits. Loss of extension ranged from 0° to 10°. Mean=3.08; S.D.— 3.76; S.E.M.=0.74

Gross Findings—Amnion layers identified up to 6 months. No intra-articular adhesions or fibrosis. Joint surfaces smooth in many specimens, again restricted to the medial TF joint.

Histology—Amnion tissue clearly stained with MABs. Amnion seems to survive with epithelial proliferation in the short term. Evidence of chronic low grade type of immune response to amniotic tissue. Neochondrogenesis marked but restricted to medial TF joint—may be due to uneven loading due to reshaping problems during surgery.

Knee Experiments—Viable Rabbit Amnion

| Period of Follow up | 1 week to 9 months. |
|---|---|
| Number of Rabbits | 29 Fatalities - 2 |
| Number Autopsied | 23 Infections - 1 |

Joint Motion—Normal ROM in majority of the rabbits. Loss of extension ranged from 0° to 10°. Mean=2.50; S.D.— 3.81; S.E.M.=0.75

Gross Findings—Amniotic tissue identified up to 4 months. No intra-articular fibrosis or adhesions. Joint surfaces smooth in majority and again a feature of the medial TF joint.

Histology—Amnion layers identified with anti-BUDR. No evidence of acute rejection observed. Neochondrogenesis prominent in the medial tibio-femoral joint in specimens studied.

Knee Experiments—Polymer Implant

| Period of Follow up | 6 weeks to 6 months, |
|---|---|
| Number of Rabbits | 7 Fatalities - None |
| Number Autopsied | 4 Infections - None |

Joint Motion—Limitation of ROM from early states. Loss of extension ranged from 15° to 30°. Mean=19.29; S.D.—5.35; S.E.M.=2.02

Gross Findings—Marked fibrosis and adhesions in joints. Polymer sheet appeared to degrade early. Joint surfaces similar to control joints.

Histology—Inflammatory response to polymer implant. No evidence of neochondrogenesis in the articular specimens studied.

Knee Experiments—Cultured Amnion Cells Injected Into Knee Joint

| Period of Follow up | 2–4 months |
|---|---|
| Number of Rabbits | 6 Fatalities - none |
| Number Autopsied | 5 Infections - 1 |

Joint Motion—Initial post-operative restriction of ROM. Good range of movement. Loss of extension ranged from 0° to 15°. Mean=4.5; S.D.=4.3

Gross Findings—Evidence of neochondrogenesis. No evidence of acute rejection.

Histology—Amnion tissue stained with MABs.

Knee Experiments—Cultured Amnion Cells On Biodegradable Beads

| Period of Follow up | 2–4 months |
|---|---|
| Number of Rabbits | 6 Fatalities - none |
| Number Autopsied | 6 Infections - none |

Joint Motion—Initial limitation of movement good. ROM after one week. Loss of extension ranged from 0° to 15°. Mean=3.0; S.D.=2.81.

Gross Findings—No intra-articular fibrosis or adhesions. Joint surface smooth in most specimens. Evidence of neochondrogenesis.

Histology—Amnion tissue stained with MABs. Low grade immune response.

The evidence suggests that neochondrogenesis is a feature of transplant joints in contrast to control and polymer implant joints. Cartilage regeneration was mainly restricted to the medial tibio-femoral (TF) joint in the specimens studied and appeared to be more prominent when viable amniotic membranes were used. Findings in some of the joint samples suggested a possibility of metaplastic changes in the amniotic tissue per se, in areas of cartilage regeneration. This would suggest that amnion undergoes a transformation to the host tissue, i.e. cartilage or tendon. Alternatively, regenerated cartilage may arise from pluripotential host stem cells in the marrow under the stimulus of specific growth factors. Against this is the lack of cartilage development in joints fitted with polymer implants.

Tendon Experiments

| Period of Follow Up | Range from 2 weeks to 3 months |
|---|---|
| Number of Rabbits | 22 Failures - 2 |
| Number Autopsied | 20 |

Controls = 6;
Human Amnion Cover = 7;
Rabbit Amnion Cover = 7

Findings:

C: Adhesions prominent, Grade 3 or 4 Tendon healed in fibrotic mass

H: Few adhesions, Grade 1 and 2 Tendon healing satisfactory

R: Minimal adhesions, Grade 1 Tendon healing satisfactory

Amniotic membranes appear to prevent adhesions after tendon surgery in the rabbit. Adhesions were minimal when rabbit allo-amnion was used. A chronic low grade immune response was noted with human amnion. Achilles and plantaris longus tendons healed well in amnion cover experiments, but in controls the tendons usually healed with adhesions.

Vascular Grafts

Blood is the conveyor of life. It carries oxygen and metabolites around the body and retrieves carbon dioxide and waste products from the functioning organs. Just as blood is the conveyor of life so the blood vessels are the highways.

With the passage of time, the arteries are narrowed by the deposition of atheroma (from the Greek, literally meaning porridge). This atheroma reduces the lumen or interal diameter of the vessels, interferring with the supply of blood to the target organs. The irregular wall of the blood vessels causes turbulence in blood flow and predisposes the blood vessels to the deposition of more blood clots and atheroma. A number of factors are known to predispose to the deposition of atheroma and include hypertension, smoking, lack of exercise and raised levels of fat within the blood. The consequences of impaired blood supply due to narrowing of the arteries may be extreme:

should the blood supply to the brain be interrupted, then the area of brain tissue supplied by that vessel will die and will lead to a stroke or cerebro-vascular accident (CVA). This will cause the areas of the body governed by that part of the brain to become inoperative leading to either paralysis, loss of speech or other such catastrophic sequelae the heart which pumps blood around the body is a muscle requiring blood supply and if the coronary arteries (so called because they are shaped like a corona or crown) are occluded then the part of the heart muscle supplied by that artery will die and the heart will pump less effectively. This is known as a myocardial infarction and its effects are known colloquially as a heart attack, which may lead to death if the blood vessels supplying the legs are occluded then the muscles which allow us to walk will receive insufficient oxygen and cramping pains will be felt by the patient on exercising. This leads to a gait typified by the ability only to walk short distances and then to stop in order to rest and achieve a decent blood supply. This condition is known as intermittent claudication (after Claudius the Emperor who had a pronounced limp).

Such cardiovascular diseases are the most common cause of death and disability in the Western World.

Therapeutic Implications

The importance of a sound vascular supply has been known to doctors for many years but it is only in the comparatively recent past that the medical profession has been able to do anything to rectify the situation. Indentifying risk factors is obviously of importance and doctors now treat patients with raised blood pressure, discourage smoking, encourage exercise and try to screen out members of the population who are at risk of having high blood fat levels. However, should the coronary arteries be occluded leading to pain in the chest which prefaces a heart attack, or the patient has severely limited exercise due to intermittent claudication, or is suffering from transient strokes, then it may be appropriate for the doctor to recommend a bypass operation.

Figure 6:
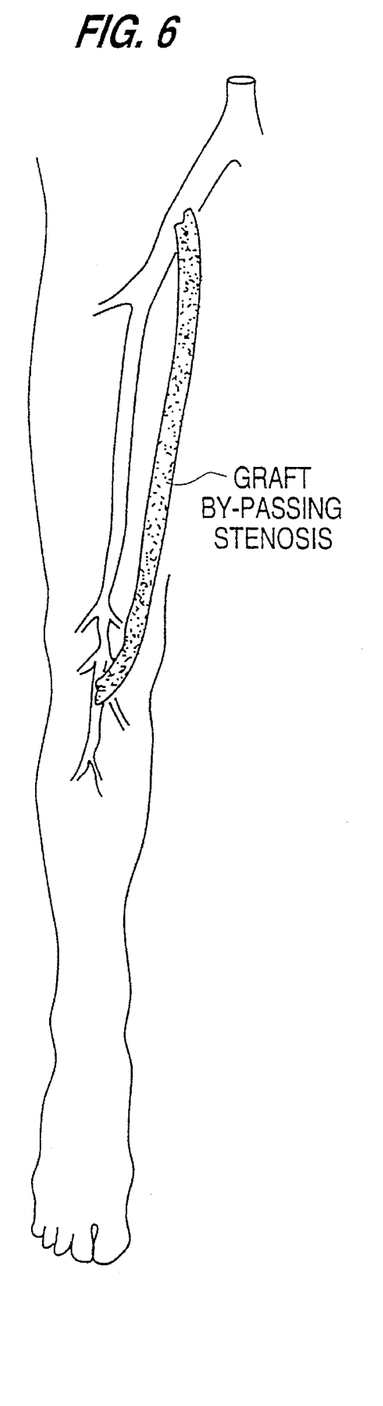
FIGS. 6 and 7 illustrate a femoro-popliteal segment bypass in humans.

In the case of intermittent claudication, one of the most commonly affected vessels is the femoral artery in the lower thigh, and it would then be usual to recommend a bypass operation from the groin to below the knee. The surgeon will make a hole or arteriotomy in the vessel above and below the narrowing or stenosis in the vessel (see FIG. 5). A bypass graft will then be sutured to these two arteriotomies thereby allowing the blood to flow past the narrowing (see FIG. 6).

Figure 7:
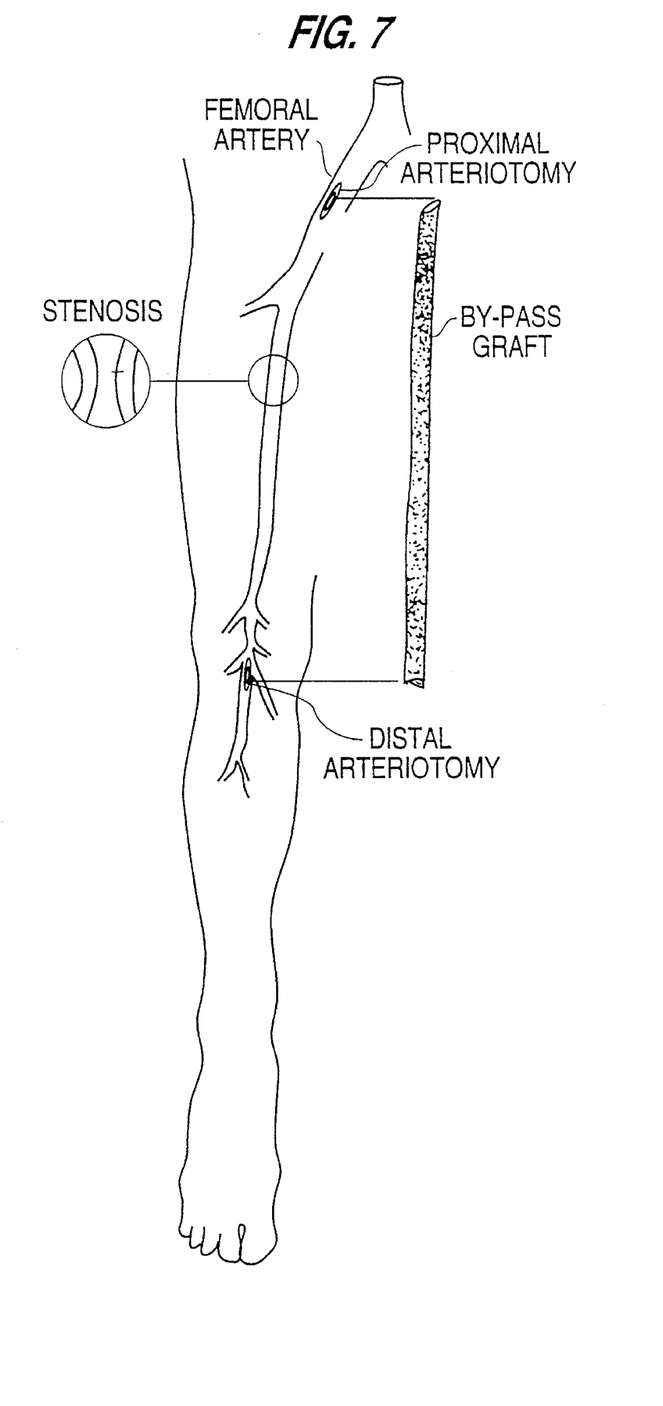

If the surgeon has established that there is a narrowing in the coronary arteries then the patient may well have to undergo a coronary artery bypass grafting operation (CABG). This is necessary where there is a critical stenosis of one or more of the vessels (see FIG. 7). The best graft currently available for this operation is the long saphenous vein in the leg. This vessel retrieves blood from the foot and returns it towards the heart but can be sacrificed as there are numerous other conduits for blood to return from the leg.

Therefore the first part of the operation involves making a long incision from the groin to the ankle and dissecting out the long saphenous vein, tying off every single branch and elevating the vein from its bed and then closing the wound. Once this has been completed the vessel must be reversed as it contains valves which ensure unidirectional flow.

The next part of the operation involves placing the patient onto a cardiopulmonary bypass machine and stopping the heart. The vein is then sutured to the diseased vessel within the heart muscle and then after restarting the heart it is sutured to the aorta (see FIG. 8). Once all the tubes to the bypass machine have been removed the reversed saphenous vein graft runs from the aorta to the coronary artery (beyond the point of stenosis) to which oxygenated blood is delivered by the heart (see FIG. 9).

A similar technique has been used to bypass diseased carotid arteries delivering blood to the brain where a vein is used to travel from the carotid artery in the neck below the point of the diseased segment and it is attached within the brain. Alternatively one of the arteries delivering blood to the face is inserted into the brain vessels.

The most commonly used synthetic materials for bypassing peripheral stenoses are teflon and woven or knitted dacron. The commercially available grafts are extremely expensive and average two hundred pounds per graft. A major advantage compared with use of the long saphenous vein is that these grafts can be taken off the shelf and are of larger diameter than the saphenous vein. However, they do not have the appropriate lining and so are predisposed to the formation of new atheroma. They very often become blocked, leading to second or even third bypass operations or maybe even the loss of the limb.

One embodiment of the present invention is to use amniotic material as a living lining for prosthetic grafts in vascular surgery. Amniotic epithelium has been shown to have unique lubricating properties (Hills 1986) and platelet activating factor (1-0-alkyl-2-acetyl-sn-glycero-3-phosphocholine) so necessary for coagulation is undetectable in amnion before delivery (Billah, 1985).

Currently prosthetic grafts are usually successful in aortic or aorto-iliac segment surgery and are able to withstand the large pressure generated. Thrombosis of the graft is not a major problem, almost certainly due to the high velocity flow. However, peripheral vascular areas such as the femoropopliteal segment or coronary artery present a major problem to grafts whether saphenous vein or prosthetic grafts of polytetrofluoroethylene and dacron.

One particular embodiment involves inculcating woven dacron grafts with a monolayer of amniotic epithelial cells grown in tissue culture. Our experiments have demonstrated that these cells can grow to confluence within five days. The cells behave in such a fashion as not to "heap" and when placed in the vascular milieu behave as a vascular endothelium and may prevent thrombosis.

The inculcated graft may be stored in a solution of phosphate buffered saline with a number of antibiotics and a shelf life of up to five years is envisaged. It is entirely feasible to produce a wide range of products for different anatomical sites and sizes.

Use of the amniotic membrane to form a lining for prosthetic vascular grafts provides, in effect, a living epithelial lining. The idea is extremely novel in that it aims to develop a composite amnion bioprosthetic implant for specific surgical uses. We have developed methods for layering the intact amnion onto the surface of prosthetic grafts in order to form a lining within the lumen.

In one procedure, tubes of amnion are produced, after carefully dissecting the sheet of amnion from the chorion. The mesenchyme is then scraped off with a razor blade leaving only the monlayer of amniotic epithelial cells. This is formed into a tube, inserted into a preformed dacron graft and sutured at either end. It is necessary to form a firm union in order to prevent aneurysmal dissection between the two layers.

Cell Culture Protocol

Reflected amniochorions from normal pregnancies are collected during elective caesarean sections in ice cold minimum essential medium with Hanks salts and buffered with HEPES. The membranes are washed with several changes of Earles balance salt solution, lacking divalent cations (EBSS) to remove blood clots abnd decidua remaining on the chorionic surface. A further incubation for fifteen minutes in EBSS is followed by manual separation of amnion from chorion. The amniotic membranes are washed three times in EBSS containing 100 units per millilitre of benzyl penicillin and 100 microgrammes per millilitre of streptomycin. The amnion is cut into pieces and each piece briefly digested in EBSS containing 0.05% trypsin and 0.02% of EDTA and antibiotics. This is followed by more prolonged incubation for thirty minutes in fresh trypsin-EDTA, with intermittent agitation to detach the epithelium. Digestion is stopped by the addition of foetal calf serum (FCS) to a final concentration of 10%. Undigested membrane is removed and amniotic cells collected by centrifugation at 400 revs per minute, followed by two washes in medium, drying to resuspension and plating.

Amniotic epithelial cells are seeded into tissue culture flasks and cultures established in RPMI 1640 medium (supplemented with 2 millimoles glutamine, 10% heat inactivated foetal calf serum and antibiotics as above) at 37° C. in 5% $CO_2$ for five days, after medium containing non-adherent cells is replaced with fresh medium and culture is continued to confluence. Approximately 1–2 hundred thousand cells may be obtained for culture from a whole membrane.

EXAMPLE 2

Sterile woven dacron grafts and grafts precoated with collagen and with an internal diameter of 6 mm were prepared as 1 cm long segments. Amniotic epithelial cells were obtained as follows:
a) directly at the time of harvesting for membranes
b) after primary passage in culture and confluence, by trypsinisation of monolayers with 0.04% trypsin and 0.02% EDTA in balance salt solution.

Amniotic cells were suspended in growth medium (RPMI 1640) with additives as above and buffered with 25 millimoles HEPES and seeded into the graft lumen. The graft was initially positioned in a vertical position and the lumen filled with the cell suspension. After five minutes of incubation, the graft segments were placed horizontally and turned 90 degrees every minute for three rotations and then through one rotation every five minutes for thirty minutes. Some of the seeded grafts were then rinsed with phosphate buffered saline and fixed with 95% alcohol for fifteen minutes at ambient temperature, while others were placed in culture medium at 37° C. for 48 hours prior to such a fixation treatment. Grafts were rinsed with distilled water and stained for two minutes with Gills haematoxillin followed by further washes in water and alcohol. Light microscopy and visual cell counts were then performed.

Initial experiments demonstrated that direct cells have a low seeding efficiency probably due to the presence of non-viable cells. However cells that have been in primary passage have the benefit of being a population of viable pure epithelial cells; since a high seeding density is required for high initial attachment density, this technique is much preferred. At seeding densities of 1.5 to 200 thousand cells/cm$^2$ and after several hours in incubation and saturation, cell attachment was achieved.

Vascular grafts prepared in this way were inserted into experimental animals to achieve successful coronary artery bypass, aorto-iliac bypass and femoro-popliteal segment bypass.

Development of Biological Artificial Kidney

The mammalian kidney functions as an elaborate filter which removes waste matter from the blood in a controlled fashion. The organ is perfused with blood laden with waste products such as urea and homeostatic mechanisms ensure that the waste products are removed and excreted in the urine but other substances such as sodium and potassium are carefully regulated, filtered and re-absorbed. One of the other important functions of the kidney is to control the volume of water in the body and hence the concentration of urine may be altered. In addition, the kidney produces a number of hormones.

One of the principal functions of the amnion is to act as a filter of toxic material being produced by the foetus during stages of its development. In particular the amnion functions as a simple "kidney" for the clearance of urea. This is especially important whilst the embryonic kidneys are developing, but the amnion retains its filtration capability even until full term.

In vitro experiments have shown that amnion cells taken in the first and second trimesters have much greater capacities to clear urea than the amnion at term.

Studies by Lingwood and Wintour (1983), in sheep, showed that the permeability of amnion to urea varied with the age of the foetus. When the foetus was less than one hundred days old, the permeability to urea was $1.718 \pm 0.485 \times 10^{-4}$ cm/sec whereas after one hundred days of gestation, the amniotic permeability fell to $0.321 \pm 0.340 \times 10^{-4}$ cm/sec. The mean permeability of amnion to water was significantly greater than the permeability to urea at all stages studied.

The most interesting finding from the work of Lingwood and Wintour is that during the last third of gestation, the ovine amnion is almost completely impermeable to the small urea molecule whilst remaining permeable to water. They concluded that in this respect the in vitro amniotic epithelium is behaving similarly to the cells of the distal convoluted tubule and the collecting duct of the mammalian kidney under the influence of arginine vasopressin. They also concluded that the amnion goes through a maturation process similar to that of many foetal tissues, especially foetal skin which is highly permeable to water and sodium early in gestation, but later becomes impermeable. Thus, this may suggest that the point in gestation at which the amnion cells are removed for culture is of critical importance.

This suggests that either the amnion cells lose their filtration capacity as they mature or the environment in the amniotic sac changes as the foetus becomes fully developed. Local changes may also occur since it has been shown that for the efficient clearance of urea in vitro, calcium is required in the bathing fluid (Casey 1986).

The permeability of amnion was not affected by the concentration of glucose in the buffer solution. This is an important feature since it has been shown that in diabetic women in whom amniotic fluid glucose concentrations are elevated, there is formation of excess amniotic fluid.

Further evidence that the placenta acts as the foetal kidney can be seen from the ability of the chorion to produce renin which is normally secreted by the adult kidney (Galen 1982, Atlas 1981, Poisner 1982).

Thus, there is good evidence to suggest that amniotic cells have the capacity to behave in a similar way to renal tubular cells in the fully developed kidney. Furthermore, amniotic cells in culture appear to retain this capacity to act as a semi-permeable membrane.

An important area of difference between amnion cells and renal tissue is the ability to absorb water. Whereas normal kidneys absorb large volumes of water through the tubular system, the amnion carefully controls the amount of fluid in the amniotic cavity and prevents excess loss from this important fluid compartment.

The permeability of foetal membranes has been studied mainly in vitro. There is evidence that the amnion probably does not operate as simple semi-permeable membrane and that the epithelial cells may be active in controlling ionic movement. High levels of adenosine triphosphatase in these cells suggests the possibility of active re-absorbtion of sodium from the fluid in the intercellular spaces. It is possible that in vivo the ammniotic membrane maintains a fine balance between the hydrostatic and osmotic forces controlling the movement of fluids. The presence of pedicels is highly suggestive of active transport. In implantation studies of the amnion with the mesenchyme toward the host, fluid appeared within the cavity in all instances (whether as a transudate or as an active exclusion is unknown).

As the foetus develops in the uterus, the surrounding amniotic fluid is initially isotonic to extracellular fluid but in both man and sheep becomes progressively hypotonic as term approaches. The sodium concentration decreases and urea and creatinine concentrations increase. Although wide variations are seen in the volume of fluid in different individuals of a particular gestational age, the composition is tightly controlled.

Abnormalities of amniotic fluid volume are associated with increased perinatal mortality and morbidity. Oligohydramnios is associated with pulmonary hypoplasia and malformations resulting from compression of the foetus, e.g. Potters syndrome. Polyhydramnios can result in premature rupture of membranes, preterm delivery, maternal dyspnoea, nausea and pain and cord prolapse. Polyhydramnios is often associated with foetal malformations and with abnormalities of maternal physiology such as diabetes mellitus, pre-eclampsia and rhesus incompatibility.

Potential Development

The amnion cells have the built in ability to function as a simple kidney by removal of waste products and control of fluid excretion. This may be sufficient in itself to use the amnion in the appropriate delivery system as an artificial kidney. It may also be possible, given the correct stimulus or the suitable environment for the cells, to enhance the basic innate ability of the amnion cells. The advantages of such a system are:
1. The use of a natural biological membrane.
2. A more compact system than is currently available for renal dialysis. In time, and with further development it should certainly be possible to produce an artificial kidney system small enough to implant within the patient.
3. An artificial kidney produced from amnion cells would be unlikely to produce damage to circulating cells and remove essential elements from the plasma in the way that current artificial kidney systems do.

As we have seen from previous work, amnion cells are capable of clearing urea and water in vivo and this has been demonstrated in vitro. Amnion cells from dissaggregated tissue culture have been coated onto non-degradable sepharose microspheres and could also be coated onto biodegradable microspheres. They are incorporated in a plasmaphoresis system and act as a filter for toxic products.

Hair Follicles

We have found that human hair follicle cells retrieved from operative skin samples may be grown with ease in an amniotic epithilial tissue culture. Thus by producing a cream or ointment or foam or suspension containing amniotic epithilial cells, to be applied to areas of alopecia, hair follicle growth and hair growth may thus be stimulated. In addition, growth factors extracted from amniotic epithelial tissue culture may be included in a cream or ointment or lotion which may be applied to areas of alopecia to stimulate hair follicle and hair growth, or growth factors isolated from amniotic epithilial tissue culture may be administered orally or by injection, either into subcutaneous, subdermal tissue or intravenously or intramuscularly to stimulate the hair follicle cells and hair. This system may also be utilised to grow endocrine cells to produce hormones, exocrine cells to produce enzymes and any other human or animal cell line.

Cosmetic Implication

We have demonstrated that amniotic epithilial tissue culture promotes the generation of collagenous tissue and amniotic epithilial cells in a lotion or cream or ointment may be applied to the skin to stimulate the production of cartilage in the host and may thus be used as a treatment for skin ageing. In addition growth factors extracted from amniotic epithilial tissue culture could be applied in a cream or lotion or ointment, or as a subdermal, subcutaneous, intramuscular or intravenous injection or taken orally for the treatment of ageing skin.

We claim:

1. A method of regenerating or replacing in vivo diseased or damaged cartilage tissue in a skeletal joint which comprises implanting into the skeletal joint an effective amount of viable human or animal amniotic cells or tissue.

2. A method as claimed in claim 1 wherein said amniotic cells or tissue comprise epithelial cells free of the mesenchyme.

3. A method as claimed in claim 1 wherein (i) live epithelial cells are harvested from fresh amniotic membrane (ii) the harvested cells are cultured; and (iii) the cultured cells are introduced into the skeletal joint.

4. A method as claimed in claim 1 wherein said amniotic cells or tissue are coated onto biologically acceptable carriers prior to implantation into the skeletal joint.

5. A method as claimed in claim 4 wherein said carriers are microspheres.

6. A method as claimed in claim 1 wherein said amniotic cells or tissue are coated onto and/or laminated with and/or infused into a suitable prosthesis prior to implantation into the skeletal joint.

7. A method as claimed in claim 1 wherein said amniotic cells or tissue are introduced directly into the skeletal joint.

* * * * *